(12) United States Patent
Metz-Stavenhagen

(10) Patent No.: US 6,719,798 B2
(45) Date of Patent: Apr. 13, 2004

(54) VERTEBRAL COLUMN SEGMENT

(76) Inventor: Peter Metz-Stavenhagen, Schlossstrasse 24, Bad Wildungen (DE), D-34537

( * ) Notice: Subject to any disclaimer, the term of this patent is extended or adjusted under 35 U.S.C. 154(b) by 0 days.

(21) Appl. No.: 10/059,731

(22) Filed: Jan. 29, 2002

(65) Prior Publication Data

US 2002/0107575 A1 Aug. 8, 2002

Related U.S. Application Data

(63) Continuation of application No. PCT/DE00/02760, filed on Aug. 16, 2000.

(30) Foreign Application Priority Data

Aug. 20, 1999 (DE) .......................... 199 39 530
Sep. 17, 1999 (DE) .......................... 199 44 682

(51) Int. Cl.$^7$ ................................. A61F 2/44
(52) U.S. Cl. ....................... 623/17.16; 606/61
(58) Field of Search .................... 623/17.11, 17.12, 623/17.13, 17.14, 17.15, 17.16; 606/61, 75, 74

(56) References Cited

U.S. PATENT DOCUMENTS

| | | | | |
|---|---|---|---|---|
| 5,514,180 A | * | 5/1996 | Heggeness et al. | ...... 623/17.16 |
| 5,849,993 A | | 12/1998 | Tada et al. | |
| 5,899,939 A | | 5/1999 | Boyce et al. | |
| 6,235,969 B1 | | 5/2001 | Stice et al. | |
| 6,277,149 B1 | * | 8/2001 | Boyle et al. | ............. 623/17.16 |
| 6,294,187 B1 | | 9/2001 | Boyce et al. | |
| 6,325,805 B1 | * | 12/2001 | Ogilvie et al. | ................. 606/75 |
| 6,383,221 B1 | * | 5/2002 | Scarborough et al. | ... 623/17.11 |
| 6,425,920 B1 | * | 7/2002 | Hamada | .................. 623/17.16 |
| 6,444,205 B2 | | 9/2002 | Dinsmore et al. | |
| 6,447,546 B1 | * | 9/2002 | Bramlet et al. | .......... 623/17.16 |
| 6,530,955 B2 | * | 3/2003 | Boyle et al. | ............. 623/17.11 |
| 6,547,823 B2 | * | 4/2003 | Scarborough et al. | ... 623/17.16 |

FOREIGN PATENT DOCUMENTS

| | | |
|---|---|---|
| DE | 19632404 | 2/1998 |
| DE | 196 32 404 A | 4/1998 |
| EP | 0 049 341 A | 4/1982 |
| WO | WO 98 05274 | 2/1998 |
| WO | WO 99 01164 | 1/1999 |
| WO | WO 00 00588 | 1/2000 |

OTHER PUBLICATIONS

Niemann, H.: "Transgene Schweine Fuer Xenotransplantate Fuer Den Menschen";Deutsche Tieraerztiliche Wochenschrift, Schaper, Hannover, DE Band 106, No. 4, Apr. 1999, pp. 141–146, XP000920828, ISSN:0012–0847 whole document.

* cited by examiner

*Primary Examiner*—Pedro Philogene
(74) *Attorney, Agent, or Firm*—Thomas R. Vigil; Welsh & Katz, Ltd.

(57) ABSTRACT

The vertebral column segment is designed for being implanted into a human vertebral column (10). The vertebral column segment comprises a vertebral body insert (42) and or comprises an intervetebral disc (22) with the associated upper and/or lower vertebral body fragment (28, 34) and/or comprises a vertebral arch (28, 30), particularly provided with the diverse extensions. According to the invention, the intervertebral disc (22) is made from a genetically manipulated animal intervertebral disc, or the vertebral body insert, the vertebral body fragments (24, 34), the vertebral arch (28, 30) and/or the extensions are made of genetically manipulated animal bones.

13 Claims, 5 Drawing Sheets

VERTEBRAL COLUMN SEGMENT

BACKGROUND OF THE INVENTION

This is a continuation of PCT/DE 00/02760, filed Aug. 16, 2000.

1. Field of the Invention

The present invention relates to a vertebral column segment for implanting into a human vertebral column.

2. Description of Related Art

Many people suffer from a diseased or damaged intervertebral disc (also called spinal disc). Genuine healing of this intervertebral disc is not possible for the intervertebral discs mainly consist of cartilaginous tissue and cannot regenerate.

The German Patent No. DE 196 32 404 A1 discloses a transplantable cartilage tissue consisting of a new extracellular matrix (ECM) that sets free matrix molecules, immunosuppressive or cell differentiating factors in response to gene manipulation, the cartilage tissue being surrounded by a semipermeable membrane. This cartilage tissue is suited for joints but not for replacing an intervertebral disc, though.

BRIEF SUMMARY OF THE INVENTION

In view thereof, it is the object of the present invention to provide a vertebral column segment for implanting into a human vertebral column that is available in sufficient quantity.

The technical solution to this object according to the invention is to form a vertebral column segment for implanting into a human vertebral column that comprises a vertebral body insert and/or an intervertebral disc with the associated upper and/or lower fragment of a vertebral body and/or a vertebral arch, more specifically provided with the diverse processes, the intervertebral disc being made from a gene manipulated animal intervertebral disc or the vertebral body insert, the fragments of the vertebral body, the vertebral arch and/or the processes being made from gene manipulated animal bones.

The present invention is based on the findings that a transgenic animal intervertebral disc and/or a transgenic animal bone, more specifically from a pig or a sheep, is in principle also suited for implantation into a human spine.

A vertebral column segment formed according to this technical teaching has the advantage that intervertebral discs and associated vertebral bodies can thus be provided as required and in sufficient quantity.

It thereby proved advantageous to genetically manipulate the corresponding transgenic animal intervertebral discs or vertebral body inserts or fragments of vertebral bodies or vertebral arches or their processes in such a manner that these elements have, as close as possible, the same blood group, more specifically the same subgroup, the same tissue structure and/or the same bone structure as the human vertebral column into which they are to be implanted.

This positively influences the successful in-growth into the human spine and the implant is unlikely to be rejected by the human body as a result thereof.

The intervertebral disc of both the human and the animal vertebral column is tightly connected to the adjacent upper or lower vertebral body and is only kept in the correct position on account of this tight connection. A once dissociated intervertebral disc proved to have difficulties in growing on again on the vertebral body; it is therefore advantageous to implant the intervertebral disc together with the vertebral body situated underneath and/or above it or at least with an appropriate fragment of vertebral body. In order to quickly grow the implant to the size wanted and/or in order for the implant to quickly grow into the human spine, the growth of the animal bone is accelerated by means of a nutrient solution and/or a growing factor. This nutrient solution may for example be hydroxylapatite (also called coral limestone) which stimulates bone formation.

To remove the diseased and damaged spinal disc, the adjacent vertebral bodies are advantageously severed with a clean cut. This also facilitates the formation of the implant. After the implant is inserted into the appropriate location in the human spine, the implant is fixated to the two parts of the divided vertebral body utilizing a clip. Such a clip is advantageously given the shape of a U and its edges are so sharp that the clip may be pressed by its free ends into the two parts of the respective one of the vertebral body.

In an alternative embodiment, the spinal disc is replaced by a vertebral body insert that is exclusively made from gene manipulated animal bone?. Although the corresponding portion of the vertebral column becomes permanently stiff as a result thereof, implantation of this vertebral body insert is less problematic.

Other examples of gene manipulation of bone, in addition to DE 19632404, are disclosed in U.S. Pat. Nos. 5,849,993, 6,235,969, and 6,444,205, the disclosures of which are incorporated herein by reference.

In an alternative embodiment, it proved advantageous to fasten the fragments of the vertebral body and/or the vertebral arch by means of at least one screw, more specifically of a so-called BioScrew or of a BioPin. This also permits to reliably secure the implant.

In a preferred development, the screw is so long and so thin that the screw extends through the vertebral arch into the vertebral body; this provides for a reliable fixation of the implant as well.

In still another preferred embodiment, the screw ends in a counterpart that is provided with a corresponding internal screw thread, the counterpart being introduced into the vertebral body from the opposite side and being kept positively locked within the vertebral body. As a result thereof, the implant is interlocked with and very reliably connected to the human spine.

Further advantages of the vertebral column segment in accordance with the invention will become apparent in the accompanying drawing and in the following description of embodiments. Also and in accordance with the invention, the features mentioned herein above and those still to be discussed can be used either individually or in any combination. The embodiments mentioned are to be considered only as illustrative and not restrictive.

DETAILED DESCRIPTION OF THE INVENTION

Figure 1:
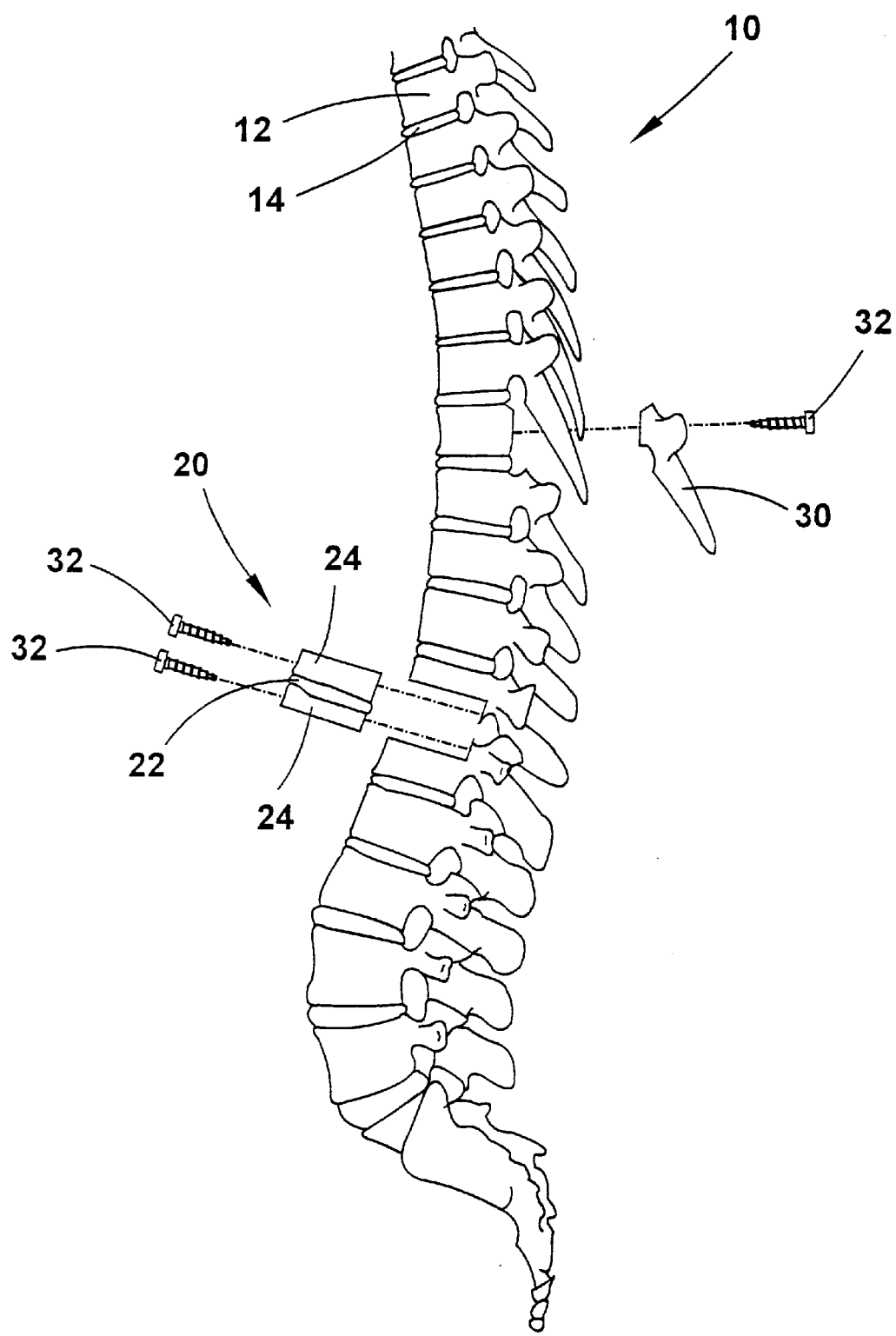
FIG. 1 is a side view of a human spine with an exploded representation of first vertebral column segments.

The human vertebral column 10 illustrated in FIG. 1 comprises a number of vertebrae 12, a spinal disc or intervertebral disc 14 being arranged between the respective vertebrae. A diseased or damaged intervertebral disc 14 can be replaced by a new intervertebral disc by removing, together with the intervertebral disc 14, a fragment (not shown) of the vertebral body 18 from the respective one of the vertebrae located above and underneath the intervertebral disc 14.

In the embodiment illustrated in FIG. 1, the vertebral column segment 20 that has been removed from the vertebral column 10 comprises a damaged intervertebral disc 14 and the respective one of the adjacent fragments (not shown) of the vertebral body 18 of vertebra 12. The fragment of the vertebral body was removed with a clean cut. Then, a new vertebral column segment 20, of the same dimension and contour, is inserted into the thus created space. This new vertebral column segment 20 is composed of a gene manipulated animal intervertebral disc 22 and of corresponding, gene manipulated fragments of vertebral body 24. The gene manipulated vertebral column segment 20 is taken from a gene manipulated pig or from a gene manipulated sheep for example. The animals are gene manipulated in such a manner that they have, as close as possible, the same blood group, and more specifically the same blood subgroup, the same tissue structure and the same bone structure as the human spine to be treated. The appropriate genetic manipulation of pigs or sheep enhances the acceptance of the vertebral column segment 20 implanted into the human vertebral column 10 since the human body will not reject this implant as a result of a foreign body response.

Figure 2:
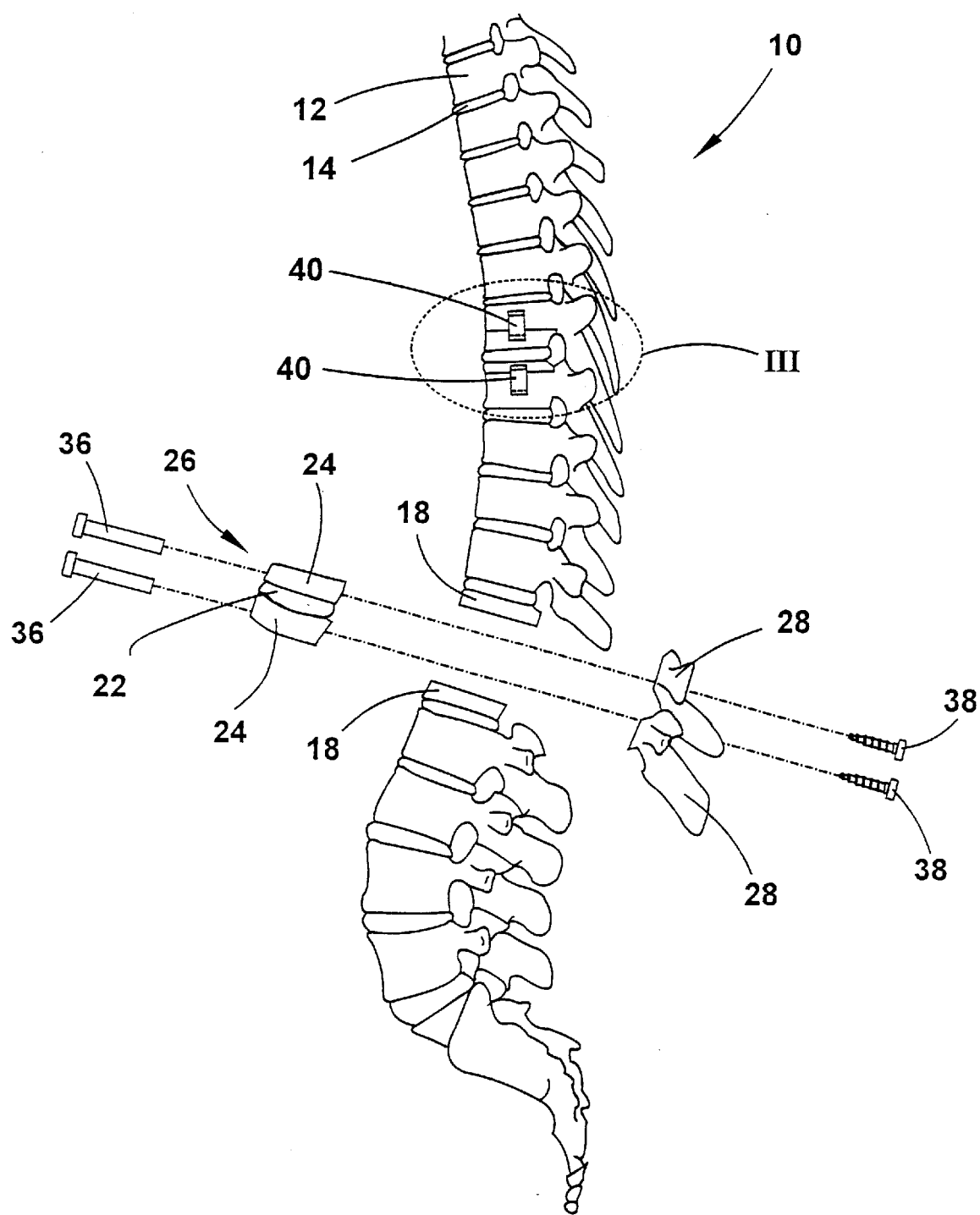
FIG. 2 is a side view of a human spine with an exploded representation of further vertebral column segments.

In the embodiment illustrated in FIG. 2, the vertebral column segment 26 extends over the entire vertebral body 18 of the vertebrae 12, the vertebral arch being severed from the vertebral body 18 together with the processes 28. As a result thereof, the intervertebral disc 14 may be implanted anew in its full size.

The vertebral column segment 20 illustrated in FIG. 1 or the vertebral arch with its processes 30 represented in FIG. 1 is screwed to an appropriate, healthy portion of vertebra 12 by means of a BioScrew or a BioPin 32. The vertebral body segment 26 illustrated in FIG. 2 is traversed in the region of its fragments 34 by sleeve-like counterparts 36, in the internal screw thread of which screws 38, which have been threaded through the vertebral arch 28, may be screwed. In this way, the vertebral body segment 26 is assembled without any damage being caused to the tracts of nerve fibers running in the vertebral column 10.

The thus assembled vertebral column segment 26 is then connected to the healthy vertebral body 18 by means of U-shaped clips 40. As can better be surveyed from FIG. 3, the clip 40 is pressed into the fragment of the vertebral body of the implant by its sharp-edged leg, whereas the other leg of the U-shaped clip 40, which is sharp-edged as well, is pressed into the vertebral body 18 of vertebra 12, thus maintaining the implanted vertebral body segment 26 in the position wanted. According to requirement, one, two or three such clips 40 may be distributed on the periphery of vertebral body 18.

The fragment of the vertebral column obtained from the respective pig or sheep may not have the size required for the human vertebral column 10. For that reason, the vertebral column segment taken from the respective animal is grown in laboratories to the size wanted by means of growth accelerators. Such growth accelerators may be hydroxylapatite (coral limestone) and/or a growing factor for example. Hydroxylapatite is for example thereby applied to the fragment of is vertebral body and is soaked with a growing factor such as a transforming growing factor or a bone morphogenetic protein. After the thus accelerated growth of the bone (fragment of vertebral body) has provided an implant of sufficient size, the implant may be implanted into the vertebral column.

Figure 3:
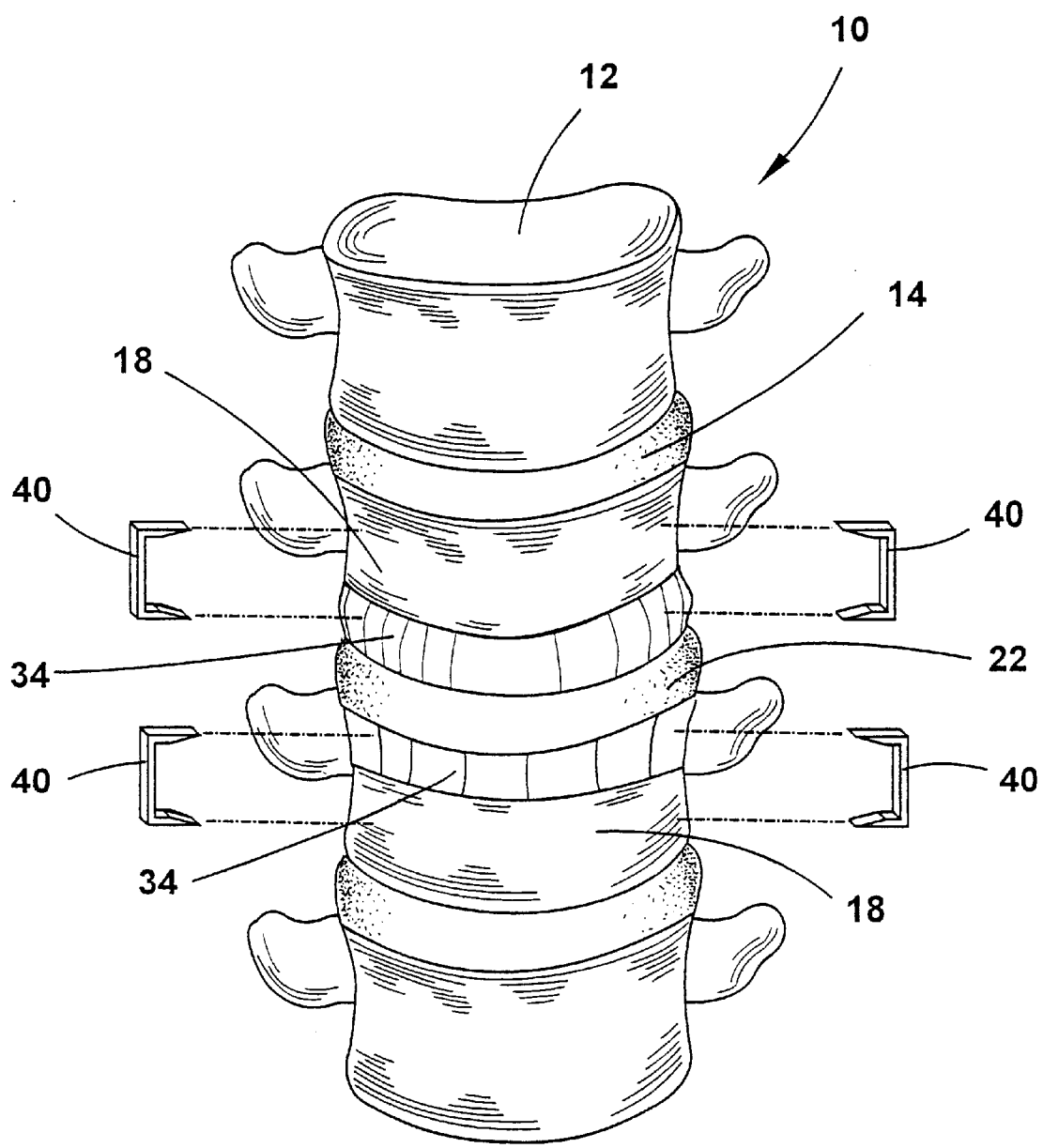
FIG. 3 is a back view of a human spine with an exploded representation of a vertebral column segment according to the invention and with an exploded representation of clips.
Figure 4:
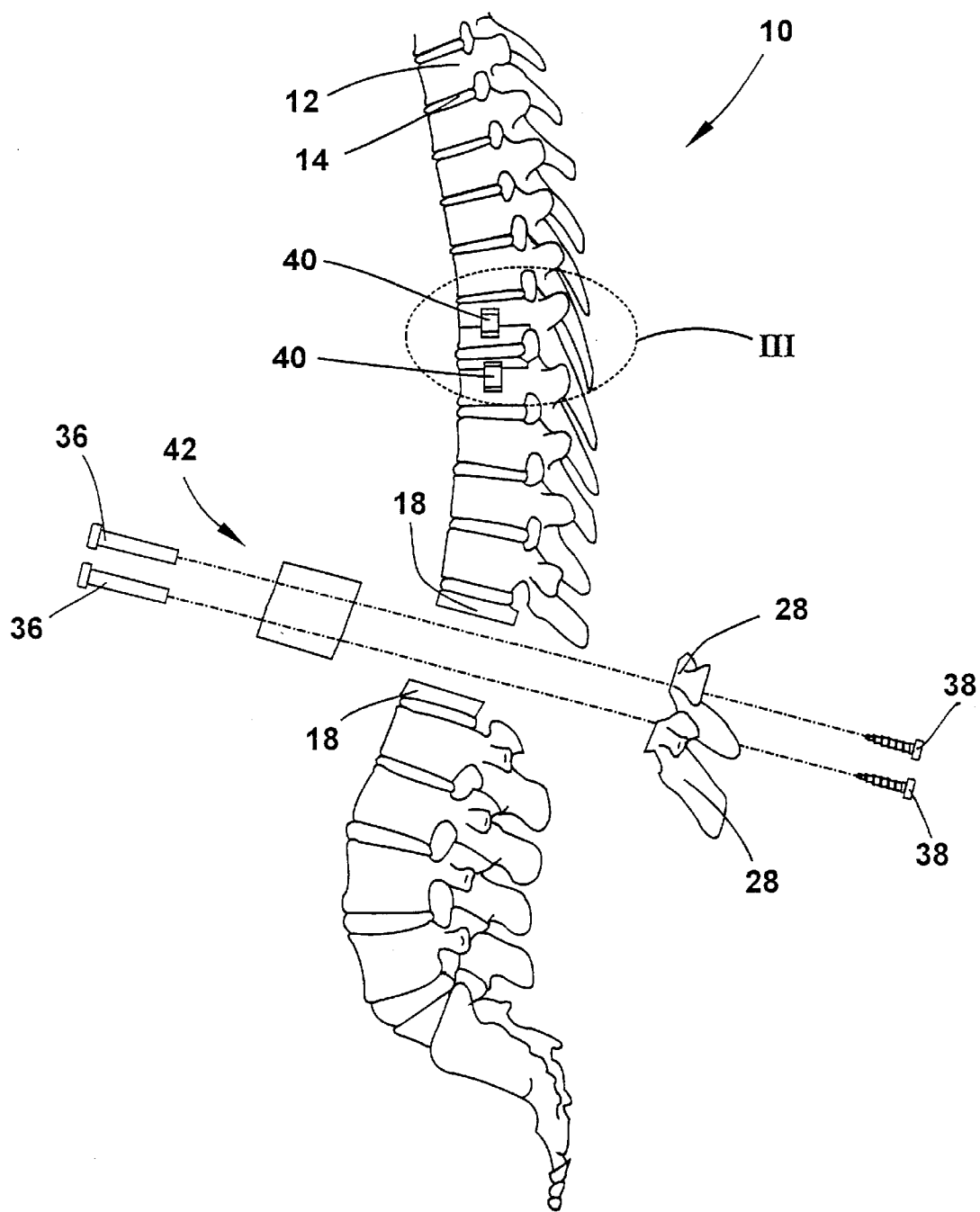
FIG. 4 is a side view of a human spine with an exploded representation of another vertebral column segment.
Figure 5:
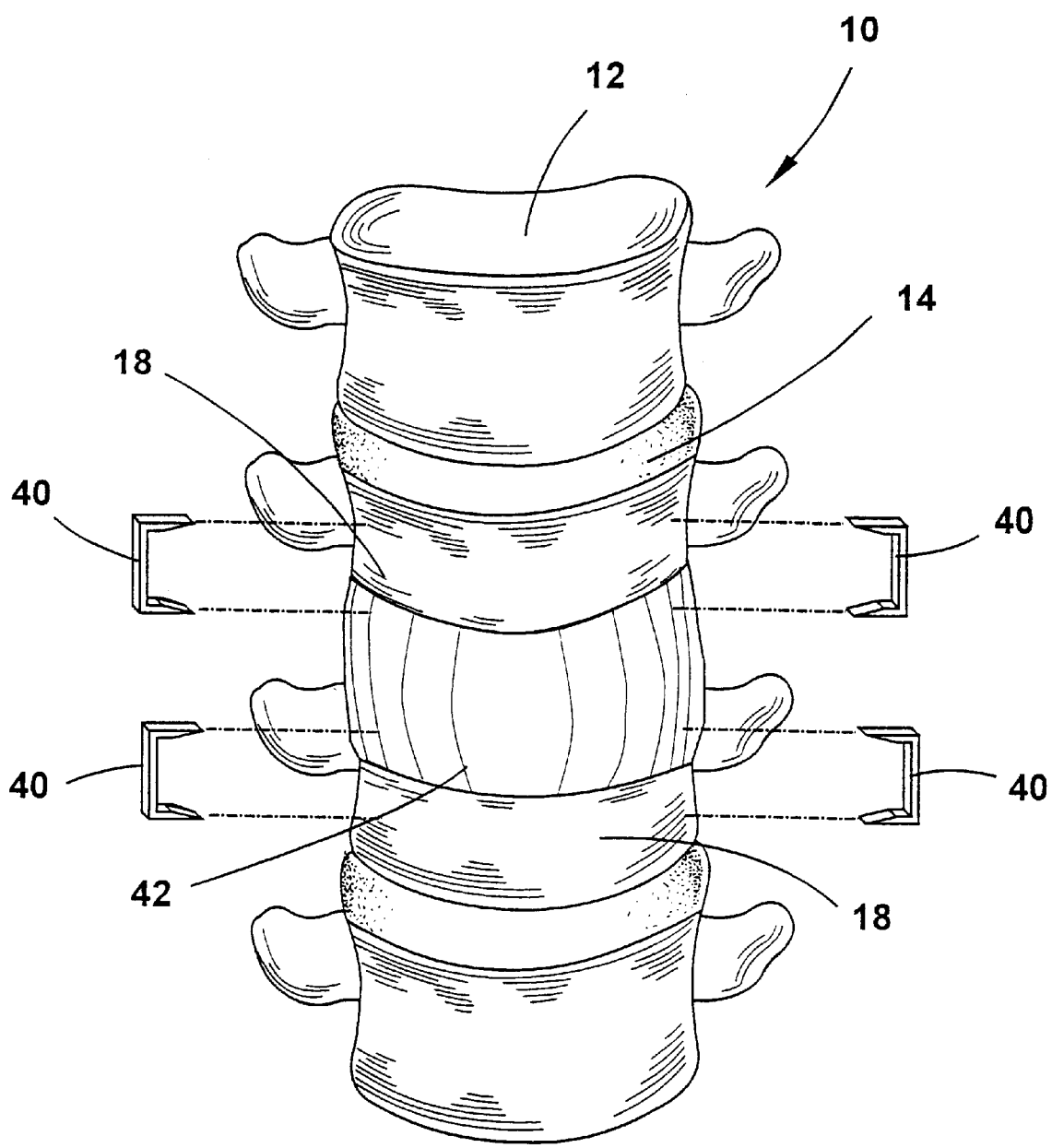
FIG. 5 is a back view of a human spine with a vertebral column segment according to the invention and with an exploded representation of clips.

The embodiment illustrated in the FIGS. 4 and 5 differs from the one represented in the FIGS. 1 and 3 in that the vertebral column segment is a vertebral body insert 42 that is exclusively made from bones which have been gene manipulated in the manner described herein above, the vertebral body insert being inserted at the location where the spinal disc was removed either in the manner described herein above or by means of clips 40. The vertebral body insert 42 and the adjacent fragments of vertebral body 18 will grow together in a manner well known in the art. This portion of the vertebral column thereby becomes stiff. In case of need, further portions of a bone may be arranged, more specifically screwed, on the vertebral body insert 42.

| Listing of Numerals | |
|---|---|
| 10 | vertebral column |
| 12 | vertebra |
| 14 | intervertebral disc |
| 16 | fragment of vertebral body |
| 18 | vertebral body |
| 20 | vertebral column segment |
| 22 | animal intervertebral disc |
| 24 | fragment of vertebral body |
| 26 | vertebral column segment |
| 28 | vertebral arch with processes |
| 30 | vertebral arch with processes |
| 32 | BioScrew |
| 34 | fragment of vertebral body |
| 36 | counterpart |
| 38 | screw |
| 40 | clip |
| 42 | vertebral body insert |

I claim:

1. A vertebral column segment for implanting into a human vertebral column (10) comprising one of a vertebral body insert (42) or an intervertebral disc (22) with one of an associated or lower fragment (24, 34) of one of a vertebral body or a vertebral arch (28, 30), the intervertebral disc (22) being made from one of a gene manipulated animal intervertebral disc, or vertebral body insert (42), or fragments (24, 34) of the vertebral body, the vertebral arch (28, 30) and one of the upper or lower fragment (24, 34) of vertebral body or the vertebral body insert (42) being fastened to the human vertebral column (10) by means of a clip (40).

2. The vertebral column segment of claim 1, characterized in that the clip (40) is U-shaped and designed in such a manner that the edges of its free legs are so sharp that the clip (40) can be pressed into one of the fragment (24, 34) of vertebral body or the vertebral body insert (42) on one side and into an adjacent vertebral body (18) of the human vertebral column (10) on the other side.

3. The vertebral column segment of claim 1 characterized in that one of the animal bone or the animal intervertebral disc (22) is genetically manipulated to create an animal bone or an animal intervertebral disc (22) having a bone structure similar to the bone structure of the human vertebral column (10) into which the vertical column segment is to be implanted.

4. A vertebral column segment for implanting into a human vertebral column (10) comprising one of a vertebral body insert (42) or an intervertebral disc (22) with one of an associated upper or lower fragment (24, 34) of one of a vertebral body or a vertebral arch (28, 30), the intervertebral disc (22) being made from one of a gene manipulated animal intervertebral disc, or vertebral body insert (42), or fragments (24, 34) of the vertebral body, or vertebral arch (28, 30) and one of the upper or lower fragment (24, 34) of one of the vertebral body or the vertebral arch (28, 30) can be fastened to the human vertebral column (10) by means of at least one screw (32, 38).

5. The vertebral column segment of claim 4, characterized in that the screw (38) is so long and so thin that the screw (38) extends through the vertebral arch (28) into vertebral body (18).

6. The vertebral column segment of claim 5, characterized in that the screw (38) ends in a counterpart (36) that is provided with an appropriate internal screw thread, said counterpart being positively locked in vertebral body (18).

7. The vertebral column segment of claim 4 characterized in that one of the animal bone or the animal intervertebral disc (22) is genetically manipulated to create an animal bone or an animal intervertebral disc (22) having a bone structure similar to the bone structure of the human vertebral column (10) into which the vertical column segment is to be implanted.

8. A vertebral column segment for implanting into a human vertebral column (10) comprising one of a vertebral body insert (42) or an intervertebral disc (22) with one of an associated upper or lower fragment (24, 34) of one of a vertebral body or a vertebral arch (28, 30), the intervertebral disc (22) being made from one of a gene manipulated animal intervertebral disc, or vertebral body insert (42), or fragments (24, 34) of the vertebral body, or vertebral arch (28 30) and one of the vertebral body insert (42) or the fragment (24, 34) of one of the vertebral body or the vertebral arch (28, 30) are provided with a planar contacting surface for abutting on the human vertebral column (10).

9. The vertebral column segment of claim 8, characterized in that the gene manipulated animal bones are formed from the bone of one of a pig or a sheep.

10. The vertebral column segment of claim 8, characterized in that the animal intervertebral disc (22) is formed from an intervertebral disc of one of a pig or a sheep.

11. The vertebral column segment of claim 8, characterized in that the growth of the animal bone is accelerated by means of one of a nutrient solution or a growing factor.

12. The vertebral column segment of claim 8 characterized in that one of the animal bone or the animal intervertebral disc (22) is genetically manipulated to create an animal bone or an animal intervertebral disc (22) having a bone structure similar to the bone structure of the human vertebral column (10) into which the vertical column segment is to be implanted.

13. A vertebral column segment for implanting into a human vertebral column (10) comprising one of a vertebral body insert (42) or an intervertebral disc (22) with one of an associated upper or lower fragment (24, 34) of one of a vertebral body or a vertebral arch (28, 30), the intervertebral disc (22) being made from one of a gene manipulated animal intervertebral disc, or vertebral body insert (42), or fragments (24, 34) of the vertebral body, or vertebral arch (28, 30), and one of the animal bone or the animal intervertebral disc (22) is genetically manipulated to create an animal bone or an animal intervertebral disc (22) having a bone structure similar to the bone structure of the human vertebral column (10) into which the vertical column segment is to be implanted.

* * * * *